(12) United States Patent
Kressner et al.

(10) Patent No.: US 7,917,982 B2
(45) Date of Patent: Apr. 5, 2011

(54) ELECTRIC TOOTHBRUSH AND CHARGING UNIT

(75) Inventors: Gerhard Kressner, Altenstadt (DE); Martin Haas, Eschborn (DE)

(73) Assignee: Braun GmbH, Kronberg (DE)

( * ) Notice: Subject to any disclaimer, the term of this patent is extended or adjusted under 35 U.S.C. 154(b) by 594 days.

(21) Appl. No.: 12/064,588

(22) PCT Filed: Aug. 22, 2006

(86) PCT No.: PCT/EP2006/008230
§ 371 (c)(1),
(2), (4) Date: Feb. 22, 2008

(87) PCT Pub. No.: WO2007/022949
PCT Pub. Date: Mar. 1, 2007

(65) Prior Publication Data
US 2008/0216258 A1    Sep. 11, 2008

(30) Foreign Application Priority Data
Aug. 25, 2005   (DE) .......................... 10 2005 040 136

(51) Int. Cl.
*A61C 17/22*   (2006.01)
(52) U.S. Cl. .......................................... 15/22.1; 310/50
(58) Field of Classification Search ................... 15/22.1, 15/22.2, 22.4, 23, 28; 310/50
See application file for complete search history.

(56) References Cited

U.S. PATENT DOCUMENTS

| | | | | |
|---|---|---|---|---|
| 3,379,906 A | * | 4/1968 | Spohr | 310/50 |
| 3,577,579 A | * | 5/1971 | Duve et al. | 15/22.1 |
| 4,991,249 A | * | 2/1991 | Suroff | 15/22.2 |
| 5,421,726 A | * | 6/1995 | Okada | 433/216 |
| 2003/0115695 A1 | | 6/2003 | Lev et al. | |
| 2003/0204925 A1 | | 11/2003 | Hall et al. | |

FOREIGN PATENT DOCUMENTS

| | | | |
|---|---|---|---|
| CH | 566 900 | | 9/1975 |
| DE | 42 01 091 | | 2/1993 |
| DE | 199 40 369 | | 5/2002 |
| DE | 103 53 715 | | 6/2005 |
| EP | 0 603 978 | | 12/1993 |
| JP | 11-318952 | * | 11/1999 |
| JP | 2003-189936 | * | 7/2003 |
| WO | 97/45328 | | 12/1997 |
| WO | 02/45919 | | 6/2002 |
| WO | 2004/024022 | * | 3/2004 |
| WO | 2004/054467 | | 7/2004 |
| WO | 2005/000149 | | 1/2005 |

* cited by examiner

*Primary Examiner* — Mark Spisich
(74) *Attorney, Agent, or Firm* — John P. Colbert

(57) ABSTRACT

A handpiece of an electric toothbrush having a housing in which a drive unit is received. The housing has a forward or rearward housing opening adapted to be closed by a cover in a preferably moisture- and liquid-proof manner, with snap-action detent elements provided on the housing and/or the cover for locking the cover on the housing with a snap action. A combination of snap-fitting and threaded engagement releases the snap-fitting engagement between the cover and the housing.

18 Claims, 3 Drawing Sheets

ELECTRIC TOOTHBRUSH AND CHARGING UNIT

TECHNICAL FIELD

This application relates to an electric toothbrush, as well as a charging unit for such a toothbrush.

BACKGROUND

A handpiece of an electric toothbrush is known, for example, from DE 199 40 369 C2. Regularly accommodated in the housings of the handpieces of electric toothbrushes are, in addition to the electric motor of the drive unit, batteries or rechargeable batteries for supplying power to the drive unit, which means that the housing has to be opened in order to be able to remove and replace the batteries or rechargeable batteries. For this purpose it is known to provide on the rearward end of the housing remote from the toothbrush head a housing opening which can be closed with a housing cover. It is also known for provision to be made on the forward end close to the toothbrush head for a housing cover which closes a housing opening through which the drive unit can be inserted from above into the housing. However, such a housing cover on the top side of the handpiece has to be securely connected with the housing by frictional and/or positive engagement in order to be able to absorb the cleaning forces introduced via the brush tube and ensure a moisture- and liquid-proof closure of the housing also under load. In this arrangement, the brush tube is coupled to the housing cover, the drive train then extending from the drive unit accommodated in the housing through the housing cover and the brush tube to the brush head. It is also known to lock such a forward-end housing cover in the region of the drive train securely to the housing by means of snap-action detent elements in order to be able to absorb the forces introduced. However, such a snap-fit connection makes it difficult to release the cover again, for example in order to be able to remove the drive unit or batteries or rechargeable batteries accommodated in the housing.

SUMMARY

One aspect of the invention features a handpiece of an electric toothbrush with a stable and firm connection between the housing and the cover, such that said connection does not become disconnected unintentionally but is easy to disconnect when required. An improved charging unit for the handpiece is also described.

As described herein, provision is made between the cover and the housing for a combination of snap-fit and threaded engagement for releasing the snap-fit connection. Provision is made on the housing and/or the cover for at least one draft engagement surface (e.g., draft taper or draft curve) ascending relative to the housing longitudinal axis, by means of which the cover can be unseated from the housing axially by twisting it about the housing longitudinal axis to release the detent elements. The draft taper or draft curve allows a threaded or snap-fit engagement between the cover and the housing and effects, for releasing the snap-fit engagement, a translation of a rotational movement of the cover into an axial movement of the same like a threaded joint. The detent elements can be disengaged in a power-saving manner by twisting the cover and they are forced to unlock by way of a constrained guidance having a screw-threaded engagement. The combination of snap-fit engagement of the cover with the housing and the draft taper or draft curve allowing a screw-threaded engagement of the detent elements for detaching the cover by twisting the same enables a firm connection between the cover and the housing to be established for transmitting high cleaning forces while enabling a comparatively power-saving unlocking of the snap-fit connection.

In some examples the draft taper or draft curve is advantageously formed on the housing by the housing edge surrounding the housing opening and on the cover by the seating surface, such as the cover edge, sitting on the housing edge, or vice versa. In some cases the housing edge surrounding the housing opening extends in a plane or curved area inclined relative to the housing longitudinal axis. Hence the forward or rearward end of the housing closed by the cover is, for example, beveled so that, given a substantially circular cross-section of the housing, the housing edge and the cover edge sitting thereon are elliptical in shape.

The inclination of the plane or curved area defined by the housing edge can generally vary by choice in order to obtain on the one hand the necessary disengagement forces and on the other hand the largest possible axial travel. As such, the inclination can be adapted to the structure of the detent elements, the fit between the cover and the housing, their materials and, where applicable, further parameters. According to an advantageous embodiment, the plane defined by the housing edge could be inclined relative to the housing longitudinal axis for example at an angle of around 65° to 85°, preferably around 75° to 80°.

By twisting the cover relative to the housing edge inclined relative to the longitudinal axis, said cover is disengaged, the detent elements are forced to unlock, and the cover is moved axially away from the housing. This is accompanied advantageously by a slight tilting movement of the cover relative to the housing, making disengagement easier for the detent elements which are advantageously distributed over the circumference of the housing.

Advantageously said draft taper or draft curve simultaneously forms a sealing surface between the cover and the housing in an axial and/or radial direction. In particular the housing edge surrounding the housing opening and the cover seating surface sitting thereon can perform this double function. If, in the previously mentioned manner, the housing edge is beveled in an inclined plane relative to the housing longitudinal axis, then on the one hand the housing can be sealed with the cover and on the other hand the cover can be unscrewed from the housing in an easy manner.

It is also possible however, alternatively or in addition, for a draft taper or draft curve of the type referred to be provided in the interior of the housing. Advantageously, the cover may have a collar suitable for insertion in the housing. Provision may be made on this collar and/or an adjacent inner wall section of the housing for at least one draft taper which extends advantageously helically around the housing longitudinal axis. In this arrangement, the draft taper engages, at the latest when the cover is twisted relative to the housing, with the collar of the cover and/or the adjacent inner wall section such that the rotational movement of the cover is translated into an axial travel and the cover is disengaged.

Advantageously, the cover seated inside the housing may have at least one draft taper or draft curve on the detent elements which lock the cover on the housing or vice versa. In particular the draft taper may be formed by the bottom edges of the corresponding detent projections and detent recesses which face away from the housing opening and, respectively, the cover edge sitting thereon. While the top edges of said detent projections and detent recesses effect the locking engagement which holds the cover in place on the housing, the opposite bottom edges of said detent projections and detent recesses may be used as a draft taper for releasing the snap-fit engagement.

Advantageously, the cover does not need to be twisted relative to the housing for it to be mounted on said housing. In some examples, the detent elements are constructed such as to be able to make snap-fitting engagement by a pure axial movement. To make seating engagement of the cover easier, the detent projections and/or the inner wall of the housing may have entry bevels on the housing edge surrounding the housing opening in order to make it easier for the detent projections to slide over the corresponding contour before they reach the undercut or recess cooperating therewith. The draft taper referred to thus effects advantageously an only single-acting screw-threaded engagement. The cover can be unscrewed over this taper but does not have to be screwed on.

To make disengagement of the snap-fit engagement easier, detent edges on corresponding detent projections and detent recesses or undercuts effecting the snap-fit engagement may extend helically or curvilinearly about the housing longitudinal axis and the cover, respectively. The detent elements may also form on the whole preferably serrate screw thread sections.

In a preferred example, the housing has only the one previously mentioned housing opening through which the drive unit and/or batteries or rechargeable batteries can be inserted into the housing. This single housing opening lies, for example, on the forward end of the handpiece close to the brush head. The accordingly single housing cover closes the housing in the region of the drive train. To make it easier to insert or remove the drive unit from the upper end of the handpiece, the housing can be constructed to be on the whole slightly conical so that it expands toward the housing opening.

To effect a moisture-proof seal between the housing and the cover it is possible generally to arrange in a manner known in the art a separate seal, in particular in the form of an O-ring, between the housing and the cover. However, according to a preferred embodiment, the housing edge surrounding the housing opening may be made from soft plastic which forms at least the sealing seat surface on which the cover edge sits.

Preferably, the housing may be injection-molded in one integral piece from two plastic components, in particular a soft plastic and a hard plastic. It will be understood, of course, that also a single-component construction of the housing, in particular from a hard plastic, is generally possible, in which case a conventional seal is preferred to an O-ring.

In order to apply the necessary sealing force between the cover and the housing and/or to ensure a wobble-free seat of the cover on the housing, the detent elements are preferably constructed such that a tensile force acts on the cover or the sealing seat. In snap-fitted condition, the detent elements hold the cover with a press fit on the housing edge surrounding the housing opening.

In order to be able to connect an exchangeable brush part to the handpiece the cover may have a coupling member, in particular a plug-in coupling member, for coupling such an attachment brush thereto. To pass the drive train through the cover, it may have, in particular in the forward end of said plug-in coupling member, a through-hole for passage of the drive train.

To enable the housing cover to be detached without the help of any tools, in some examples the charging unit for the toothbrush handpiece has locking elements for locking the cover on the charging unit in a non-rotating relationship. For example, the locking elements may comprise a recess in the charging unit housing into which the previously mentioned brush-tube plug-in coupling member of the housing cover can be inserted so that it is locked against rotation. As the result it is possible, without tongs or the like, to remove the cover of the handpiece housing by pushing the plug-in coupling member of the cover, which actually serves to mount the brush part, into the complementary recess in the charging unit. The cover can then be screwed off using the good-to-grip charging unit.

These and other features, when used singularly or in any combination or sub-combination, will become apparent not only from the claims but also from the subsequent description of a preferred embodiment and the accompanying drawings.

DETAILED DESCRIPTION

Figure 1:
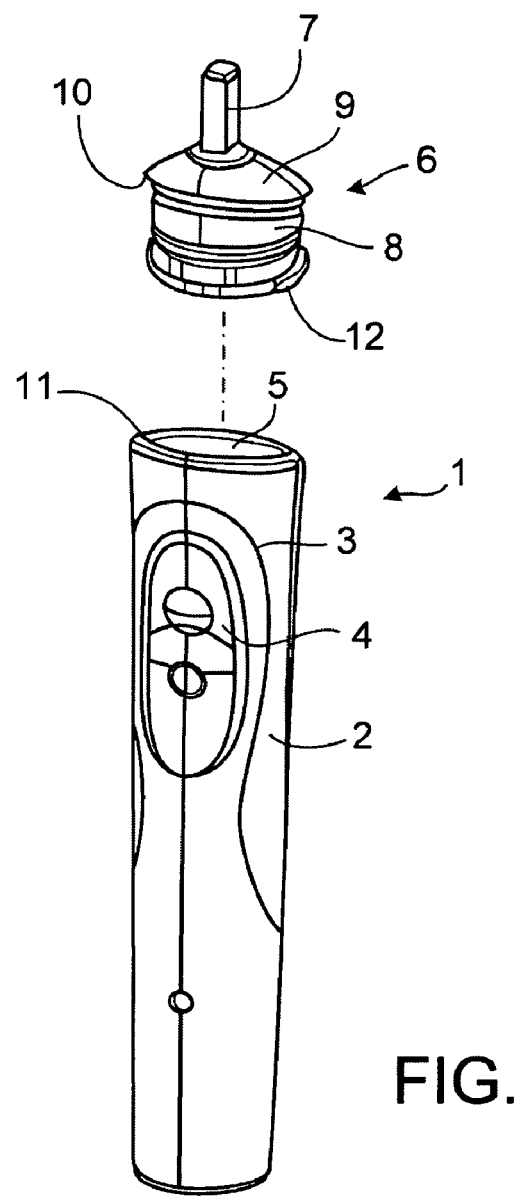
FIG. 1 is a perspective exploded view of the handpiece of an electric toothbrush, showing a housing opening at the housing forward end and the associated cover lifted off said opening.

The handpiece 1 of an electric toothbrush shown in FIG. 1 includes an approximately rod-shaped or tubular housing 2 accommodating a drive unit with an electric motor, a control unit with at least one on/off switch, and a power supply in the form of a battery or a rechargeable battery. According to a preferred embodiment of the invention, the housing 2 is injection-molded from hard plastic and soft plastic in a two-component injection-molding process. In particular the section of the housing 2 serving as the grip region 3 may be coated with a soft plastic covering. In addition, a control section 4 may be injection-molded solely from soft plastic such that the housing 2 can be depressed in this region in order to actuate the on/off switch arranged underneath.

Figure 2:
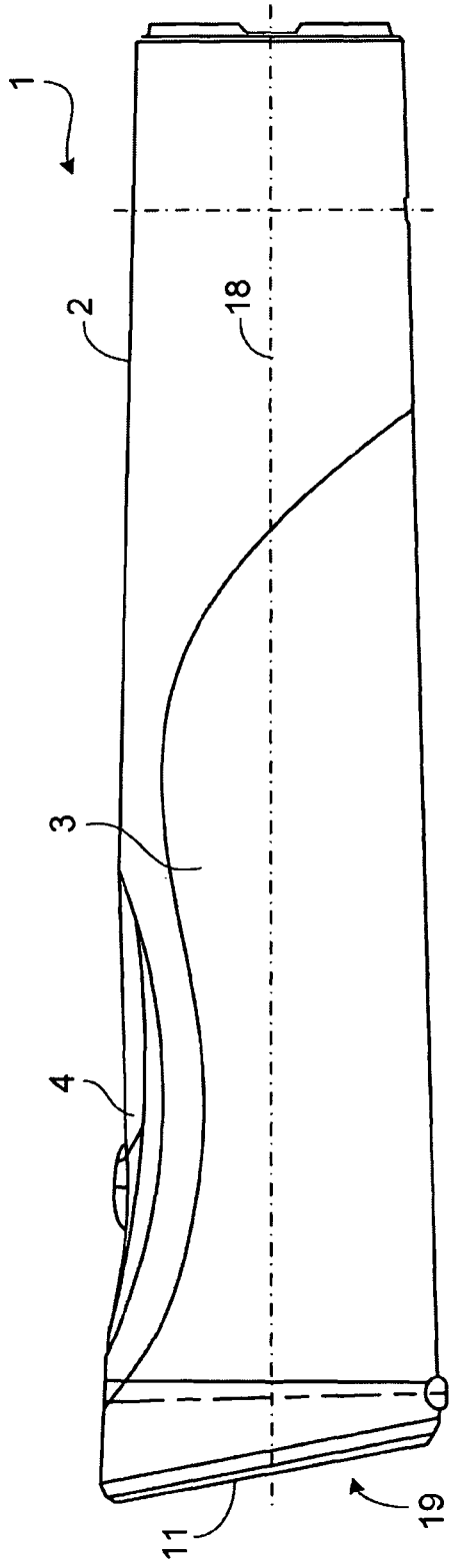
FIG. 2 is a side view of the housing of the handpiece of FIG. 1.
Figure 3:
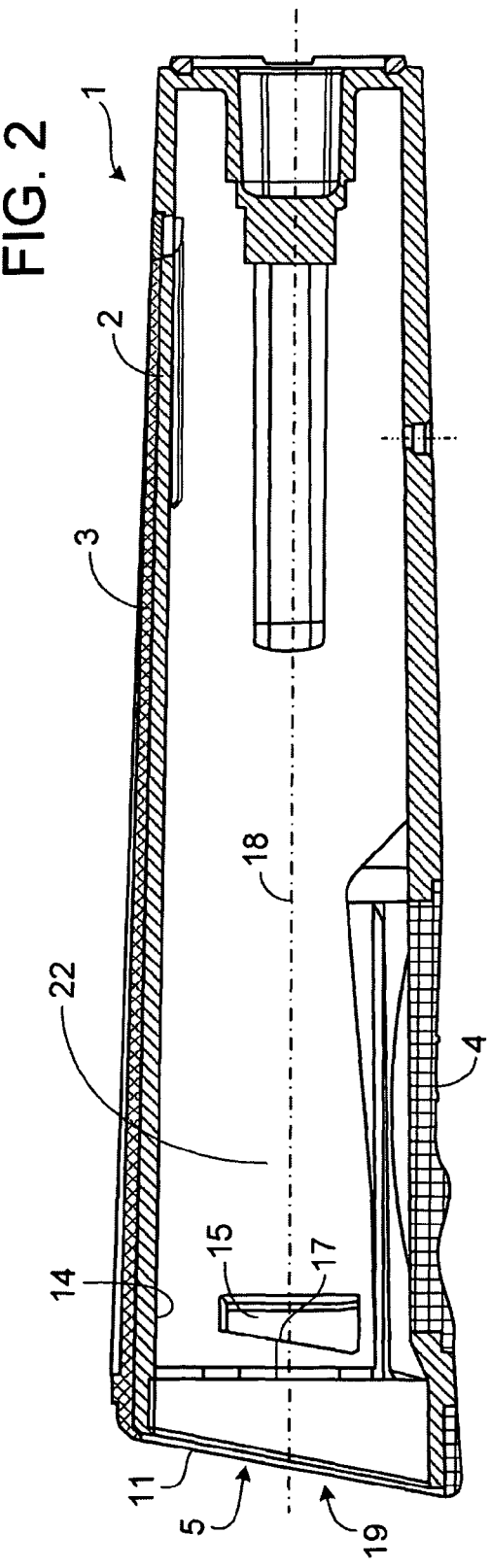
FIG. 3 is a longitudinal sectional view of the housing of FIG. 2, showing the housing edge at the housing opening, said edge being inclined relative to the housing longitudinal axis, and a detent recess in the housing inner wall.

As FIGS. 2 and 3 show, the housing 2 has only a single housing opening 5 situated on its forward end close to the attachable toothbrush head, while the opposite rearward end of the housing 2, i.e., the base of the housing 2, can be constructed to be closed. The drive unit 22, the associated control unit and the batteries or rechargeable batteries can be inserted in the housing 2 through the housing opening 5 on the forward end of the housing close to the brush head.

Figure 5:
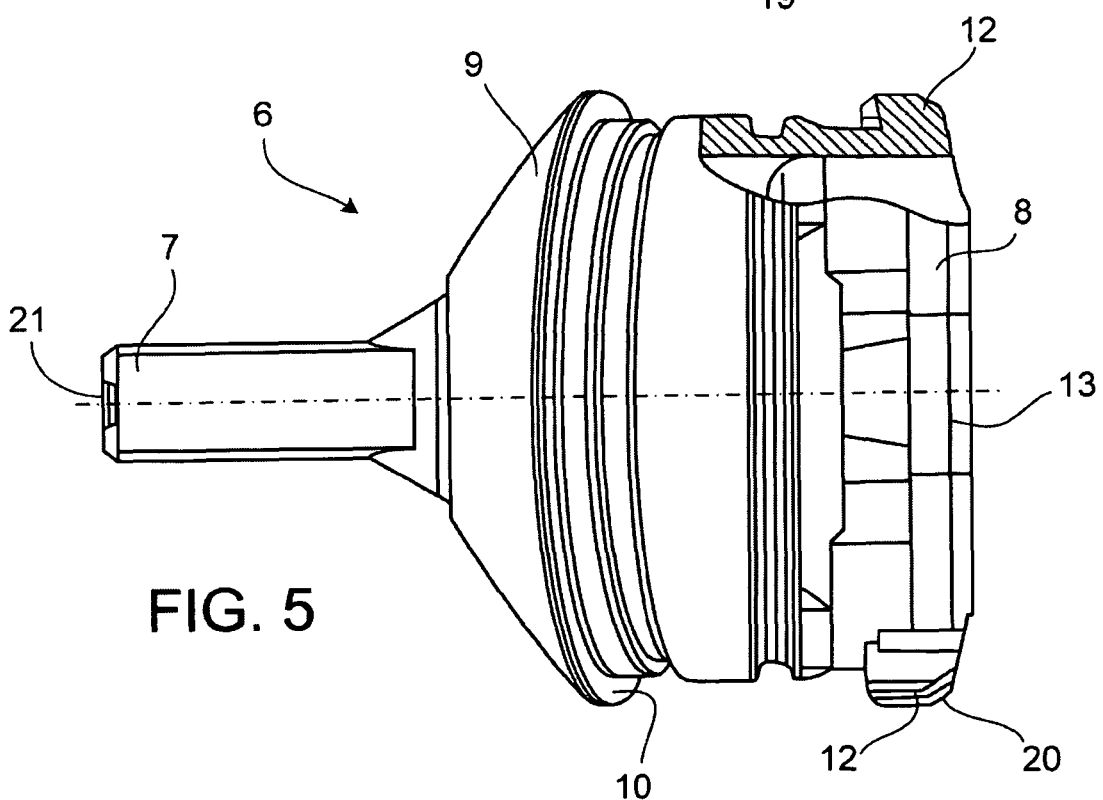
FIG. 5 is a side view, partly sectioned, of the housing cover turned through 90° compared to FIG. 4.

The housing opening 5 can be closed by a cover 6 which can be placed down onto the housing opening 5 axially. As FIGS. 1 and 5 show, the cover 6 has an extension which forms a coupling member 7 for coupling the brush tube of an attachment brush. The coupling member 7 in the embodiment shown is constructed as a plug-in coupling member such that the attachment brush merely needs to be plugged on. In the coupling member 7 provision is made for a full-length opening 21, not shown in more detail, through which the drive train, in particular its drive shaft, can be passed from the drive unit accommodated in the housing 2 to the brush head.

Because cleaning forces and cleaning torques are introduced into the cover 6 from the brush head via the coupling member 7 and the brush tube fastened thereto, said cover has to be connected sufficiently securely to the housing 2, for which purpose in the embodiment shown provision is made for frictional and positive engagement between the cover 6 and the housing 2.

The cover 6 has an essentially cylindrical collar 8 which is insertable into the housing opening 5 of the housing 2 with a snug fit. As FIG. 4 shows, the collar 8 is slightly cut back in its circumference relative to the closure section 9, which is arched or slightly lens-shaped, i.e., the cover 6 has a peripheral shoulder 10 which projects slightly beyond the collar 8 and with which the cover 6 sits snugly on the housing edge 11 surrounding the housing opening 5 when the cover 6 is pushed with its collar 8 completely into the housing opening 5.

With this configuration, the cover 6 can be mounted on the housing 2 with a snap action. For this purpose provision is made on the collar 8 for radially outwardly protruding detent projections 12 constructed in roughly rib shape, the embodiment shown providing two diametrically opposed detent projections 12 (see FIG. 5). Between the detent projections 12, the collar 8 has two opposing peripheral indents 13 so that a radially inward spring back of the collar sections bearing the detent projections 12 is promoted.

Provided on the inner wall 14 of the housing 2 in a wall section of the housing 2 made from hard plastic are detent recesses 15 which cooperate with said detent projections 12. Advantageously, said detent recesses 15 extend completely through the hard plastic shell of the housing 2 so that they are closed from the outside solely by the outer soft plastic shell of the housing 2. If the position of the detent recesses 15 is known, this enables the snapped-in detent projections 12 to be pressed in from the outside.

Figure 4:
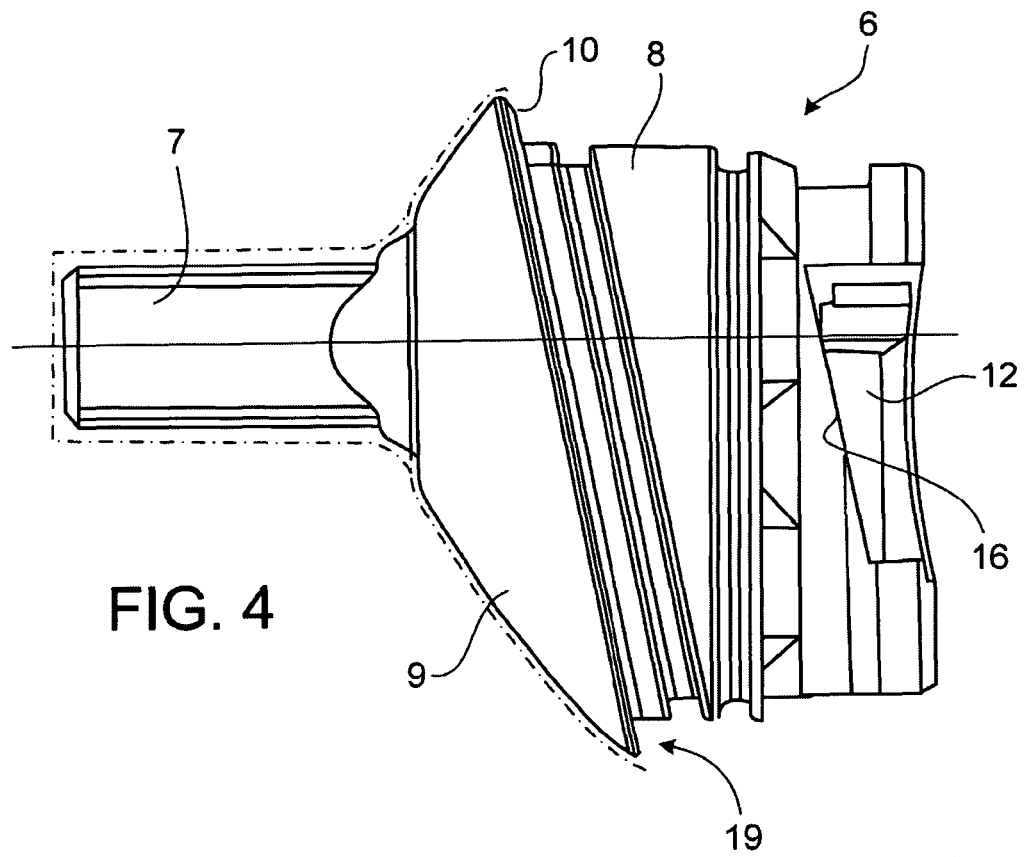
FIG. 4 is a side view of the housing cover of FIG. 1.

As FIGS. 3 and 4 show, the detent projections 12 and the detent recesses 15, respectively, have a slightly wedge-shaped contour. The detent edges 16 and 17, which effect the locking engagement and are formed by the tops and top edges, respectively, of the detent projections 12 and detent recesses 15 facing the housing opening 5 and cover top, respectively, take a slightly ascending course relative to the housing longitudinal axis 18, i.e., they do not extend at right angles to the housing longitudinal axis 18. As FIGS. 3 and 4 show, said detent edges 16 and 17 are inclined at an angle ranging from around 65° to 85°, to be more precise from around 75° to 85°, in particular around 80°. The bottom edges, i.e., the edges of the detent recesses 15 and detent projections 12 facing away from the housing opening 5, are not inclined by contrast but extend roughly at right angles to the housing longitudinal axis 18 so that the detent projections 12 and the detent recesses 15 take on a roughly wedge-shaped form.

As FIG. 5 shows, the detent edges 16 of the detent projections 12 do not project at right angles from the collar 8 but are constructed to ascend slightly upward at an angle ranging from around 5° to 15° so that the detent projections 12 secure themselves in tension within the detent recesses 15. Any unwanted opening during vigorous cleaning of the teeth is thus inhibited.

The detent recesses 15 and the detent projections 12 are spaced from the housing edge 11 and, respectively, the peripheral shoulder 10 of the cover 6 lying thereon in such a way that when the cover 6 is snap-locked, said cover is pulled by a slight press fit onto the housing edge 11 in order to obtain a tight closure of the housing 2. Advantageously, the housing edge 11 is made from soft plastic so that a sealing effect can be obtained directly through the seating engagement of the peripheral shoulder 10 on the housing edge 11. A separate sealing ring is not necessarily required.

As FIGS. 2 to 4 show, the housing edge 11 and the cover edge sitting thereon do not lie in a plane perpendicular to the housing longitudinal axis 18. Rather, the housing edge 11 and the peripheral shoulder 10 of the cover 6 sitting thereon are beveled, i.e., they extend in a plane which is inclined at an acute angle of less than 90° relative to the housing longitudinal axis 18. The angle of inclination may generally vary by choice but lies advantageously in a range from 70° to 85°. In the embodiment shown, the angle is around 79°.

The inclined housing edge 11 and the correspondingly inclined cover edge or peripheral shoulder 10 of the cover 6 combine to form a draft taper 19 by means of which the snap-fit engagement between the cover and the housing is disengageable by twisting the cover 6 like a threaded joint relative to the housing 2 about its longitudinal axis 18. Such disengagement of the snap-fit engagement is facilitated by the previously described inclination of the detent edges 16.

To make it easier to unscrew the cover 6 from the housing 2, it is possible for the charging unit for the electric toothbrush to be used advantageously as a turning tool. The coupling member 7 on the cover 6 has advantageously a non-circular outer contour which is suitable for transmitting a torque Correspondingly, the housing of the charging unit may include a complementary recess, in particular a blind hole, whose inner contour is non-circular in corresponding manner and suitable for transmitting a torque. Accordingly the handpiece 1 with the coupling member 7 on the cover 6 needs only to be inserted into this recess in the charging unit for the cover 6 to be locked against rotation on the charging unit. To release the cover from the housing it is then necessary only for the charging unit to be held securely and for the housing 2 to be turned or vice versa.

To lock the cover 6 to the housing 2, said cover needs only to be axially mounted on the housing 2 in the correct orientation without twisting and then pushed into said housing until the detent projections 12 on the collar 8 of the cover 6 snap into the detent recesses 15. To facilitate the pushing into the housing opening 5, the initially radially protruding detent projections 12 have on their bottom side entry bevels 20 (see FIG. 5) by means of which the collar 8 with the detent projections 12 can be better forced into the housing 2. In the process there develops a slight elastic deformation of the collar 8 radially inwardly and/or of the housing 2 radially outwardly until the detent projections snap into the detent recesses 15.

Figure 6:
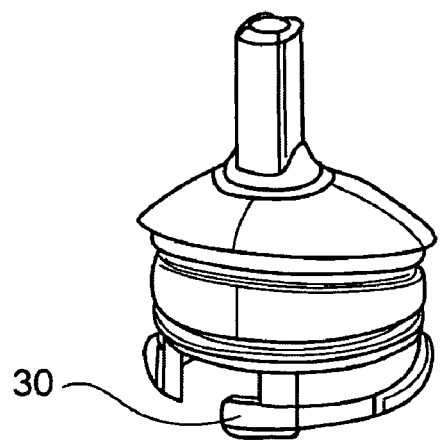
FIG. 6 is a perspective view of a cover with additional detent elements.

The cover shown in a perspective view in FIG. 6 has additional detent elements 30 suitable for snapping into additional complementary detent elements on the housing. This additional snap-fit engagement can absorb forces in the longitudinal direction of the housing. Said detent elements are constructed such that the cover is more easily released by turning in a first turning direction than in the opposite direction.

The invention claimed is:
1. An electric toothbrush handpiece, comprising:
a housing defining an opening and a longitudinal handpiece axis, the housing comprising a first locking element and a brush head drive unit contained within the housing; and
a cover comprising a second locking element, wherein the cover is configured to seal
the opening when the first and second locking elements are engaged,
wherein the housing comprises a first draft engagement surface disposed proximate an edge of the housing surrounding the opening and the cover comprises a second draft engagement surface disposed on a seating surface of the cover that sits on the edge of the housing when the locking elements are engaged, the draft engagement surfaces ascending relative to the longitudinal handpiece axis, at which engagement surface the housing and cover contact each other with the cover sealing the opening, the draft engagement surfaces arranged such that the cover is axially unseatable from the housing by twisting the cover relative to the housing about the longitudinal axis to release the locking elements.

2. The handpiece of claim 1, wherein the draft engagement surfaces form a sealing surface between the cover and the housing.

3. The handpiece of claim 1, wherein the edge of the housing extends in a plane or curved area inclined relative to the longitudinal handpiece axis.

4. The handpiece of claim 3, wherein the plane defined by the housing edge is inclined relative to the longitudinal handpiece axis by an angle between about 65" and about 85".

5. The handpiece of claim 4, wherein the plane defined by the housing edge is inclined relative to the longitudinal handpiece axis by an angle between about 75" and about 80".

6. The handpiece of claim 1, wherein the locking elements comprise detent elements, and wherein the detent elements, in a snap-fitted condition, are arranged to hold the cover with a press fit to an edge of the housing surrounding the opening.

7. The handpiece of claim 6, wherein the detent elements form serrate screw thread sections.

8. The handpiece of claim 6, wherein the housing edge comprises an entry bevel.

9. The handpiece of claim 6, wherein the detent elements comprise a detent projection with an entry bevel.

10. The handpiece of claim 6, wherein the detent elements are configured to make a snap-fitting engagement by relative axial movement of the housing toward the cover along the longitudinal handpiece axis.

11. The handpiece of claim 6, wherein the detent elements comprise edges extending in a helical or curved configuration about the longitudinal handpiece axis.

12. The handpiece of claim 1, wherein the brush head drive unit is sized to be insertable into the housing through the opening.

13. The handpiece of claim 1, wherein the housing expands in a conical configuration toward the opening.

14. The handpiece of claim 1, wherein the cover further defines a drive train opening, through which the drive unit is connectible to a brush head.

15. The handpiece of claim 1, wherein the cover further comprises an attachment brush coupling member.

16. The handpiece of claim 1, wherein the housing is molded from both a relatively hard plastic and a relatively soft plastic.

17. The handpiece of claim 1, wherein the cover comprises a collar arranged to engage an inner wall of the housing when the locking elements are engaged.

18. An electric toothbrush comprising:
a handpiece comprising:
a housing defining an opening and a longitudinal handpiece axis, the housing comprising a first locking element and a brush head drive unit contained within the housing; and
a cover comprising a second locking element, wherein the cover is configured to seal the opening when the first and second locking elements are engaged,
wherein the housing comprises a first draft engagement surface disposed proximate an edge of the housing surrounding the opening and the cover comprises a second draft engagement surface disposed on a seating surface of the cover that sits on the edge of the housing when the locking elements are engaged, the draft engagement surfaces ascending relative to the longitudinal handpiece axis, at which engagement surface the housing and cover contact each other with the cover sealing the opening, the draft engagement surfaces arranged such that the cover is axially unseatable from the housing by twisting the cover relative to the housing about the longitudinal axis to release the locking elements.

* * * * *